United States Patent [19]
Cornelius

[11] Patent Number: 5,304,116
[45] Date of Patent: Apr. 19, 1994

[54] VAGINAL CLEANSING DEVICE

[76] Inventor: Harold E. Cornelius, 2904 Loveland Ct., Bakersfield, Calif. 93309

[21] Appl. No.: 894,088

[22] Filed: Jun. 5, 1992

[51] Int. Cl.$^5$ .............................................. A61M 3/02
[52] U.S. Cl. ...................................... 604/39; 604/28; 604/279; 137/894; 137/217
[58] Field of Search ................... 604/39, 41, 150, 246, 604/259, 279, 28; 137/217, 894

[56] References Cited

U.S. PATENT DOCUMENTS

| | | |
|---|---|---|
| 540,213 | 5/1895 | Morrison . |
| 1,591,410 | 7/1926 | Spang . |
| 1,751,507 | 3/1930 | Brunette . |
| 2,283,848 | 11/1940 | Chapin . |
| 2,891,565 | 6/1959 | Mackey ............................ 137/217 |
| 2,916,042 | 12/1959 | Brady .............................. 137/217 |
| 2,957,495 | 10/1960 | Ashbrook ........................ 137/894 |
| 3,044,465 | 7/1962 | Anderson et al. . |
| 3,512,525 | 5/1990 | Crowley, Jr. . |
| 3,533,409 | 4/1968 | Greer . |
| 3,572,338 | 3/1971 | Murray, Jr. . |
| 4,000,742 | 1/1977 | DiGiacomo . |
| 4,386,928 | 6/1983 | Hart . |
| 4,642,100 | 2/1987 | Kabbaby ......................... 604/150 |
| 4,811,753 | 3/1989 | Bethune ........................... 137/217 |
| 4,950,231 | 8/1990 | Liu . |

FOREIGN PATENT DOCUMENTS 0482303  4/1992  European Pat. Off. ............. 604/39

Primary Examiner—Randall L. Green
Assistant Examiner—Bob Clarke
Attorney, Agent, or Firm—Lyon & Lyon

[57] ABSTRACT

An improved vaginal cleansing device comprising a T-shaped coupling, a first valve, a venturi, a second valve, concentrate reservoir, a solution delivery tube, and an applicator nozzle. The T-shaped coupling is interposed between a water source line and a shower head and diverts water to the first valve. The first valve controls the flow of water through the cleansing device and, when open, delivers water to the venturi. The venturi drafts concentrate from the concentrate reservoir under the control of the second valve and delivers either water or a mixture of water and concentrate to the solution delivery tube, and the solution delivery tube delivers the water or mixture to the applicator nozzle.

3 Claims, 4 Drawing Sheets

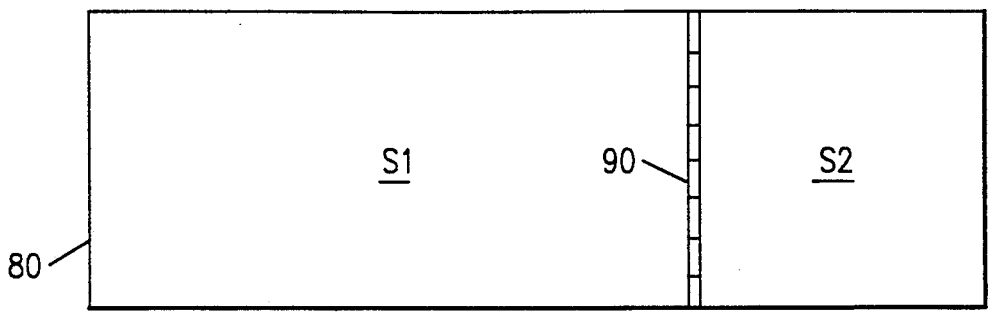
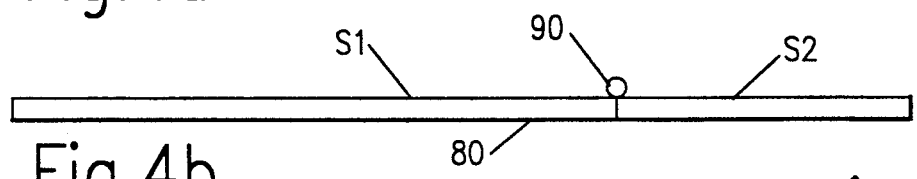
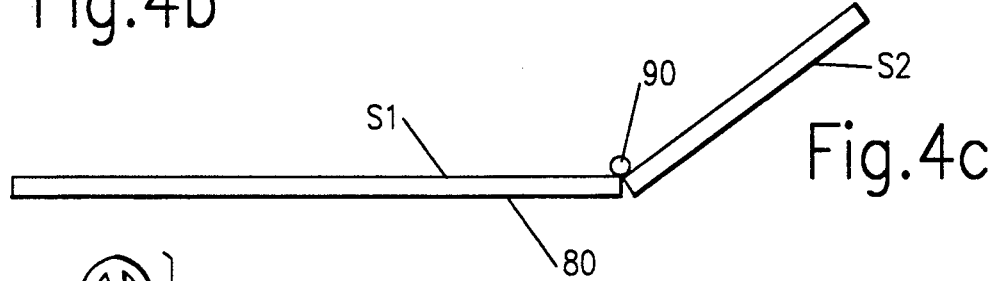
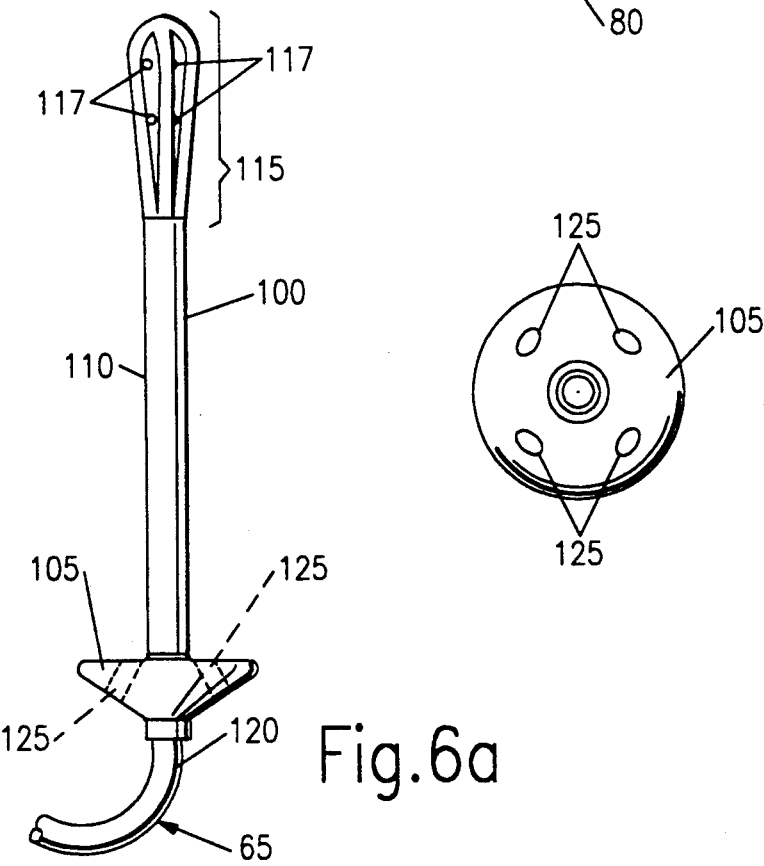
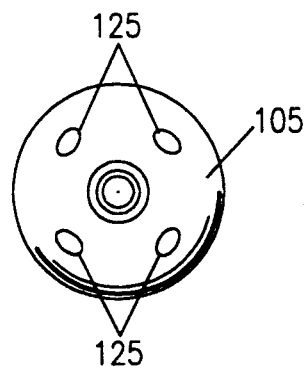

VAGINAL CLEANSING DEVICE

BACKGROUND OF THE INVENTION

The field of the invention is feminine hygienic devices of the type used for vaginal irrigation and cleansing.

Recent attention has been directed toward the development of an improved vaginal irrigation and cleansing device of a type which may be temporarily or permanently coupled to the plumbing of a private home. However, despite this attention those skilled in the art have failed to provide a cleansing device which satisfies a number of basic requirements for use in a private home. Specifically, the efforts of those skilled in the art have failed to produce a device which (1) is inexpensive, (2) may be readily incorporated into the plumbing of a home without interfering with the function of existing plumbing fixtures, (3) is capable of providing a cleansing solution comprising either pure water or a mixture of water and concentrate, (4) is capable of delivering the cleansing solution at a safe yet sufficient pressure to insure proper cleansing action, and (5) is capable of delivering the cleansing solution over a variable controlled temperature range without employing an electrical heating apparatus.

SUMMARY OF THE INVENTION

The present invention is directed to an improved vaginal cleansing device which meets the requirements set forth above. To this end, a compact vaginal cleansing device which is adapted to be interposed between a shower head and an associated water source line is provided. An exemplary embodiment of the invention employs a T-shaped coupling for diverting a portion of the flow of water between the water source line and the shower head, a venturi for drafting a concentrate solution from a concentrate reservoir and mixing the concentrate solution with the diverted water flow, two valves for controlling the flow of water and concentrate solution through the cleansing device, and a solution delivery tube for delivering a cleansing solution comprising either pure water or a mixture of water and concentrate to an applicator nozzle.

The T-shaped coupling is adapted to be interposed between a shower head and an associated water source line, the water source line providing a flow of water to the shower head, and the T-shaped coupling being adapted to divert a portion of the water flowing from the source line to a first valve. The first valve controls the flow of water through the cleansing device and, when open, delivers water to the venturi. The venturi drafts a concentrate solution from the concentrate reservoir under the control of a second valve and delivers either pure water or a mixture of water and concentrate solution to the solution delivery tube. The solution delivery tube receives the cleansing solution from the venturi and delivers the cleansing solution to the applicator nozzle, which is adapted to pass the cleansing solution into the user's vagina.

In use, the temperature of the cleansing solution is controlled in a conventional manner by adjusting the temperature of the water exiting the associated shower head. Thus, the need for additional electrical heating elements is eliminated. Further, a user of the vaginal cleansing device described above may adjust the temperature of the cleansing solution to a desired level prior to commencing the flow of solution through the cleansing device. Importantly, this allows the user of the cleansing device to position the applicator nozzle of the cleansing device within her vagina prior to commencing the flow of the cleansing solution.

In a preferred form, the vaginal cleansing device further comprises a visually attractive casing assembly which comprises a plurality of compartments, one compartment providing an enclosed area for storing the solution delivery tube and the applicator nozzle between uses, and another compartment comprising the concentrate reservoir.

In another preferred form, the tubing network further comprises a floating ball vacuum breaking device which is deployed adjacent to the water inlet port of the venturi. The vacuum breaking device insures complete drainage of the solution delivery tube and nozzle by allowing air to enter the tubing network after the cleansing device is turned off by placing the first valve in the closed position. In addition, the vacuum breaking device functions to prevent any siphoning of concentrate from the concentrate reservoir in the event of an unexpected interruption in the flow of water through the cleansing device. Thus, if the flow of water through the cleansing device is unexpectedly interrupted, pure concentrate will not be delivered to the user's vagina.

In still another preferred form, the first and second valves comprise a unitary valve assembly and are controlled by a common stem. Specifically, the first valve comprises a first half turn valve which is fully open from 90 to 180 degrees, and the second valve comprises a second half turn valve which is fully open only at 180 degrees.

Accordingly, it is an object of the present invention to provide an improved vaginal cleansing device.

BRIEF DESCRIPTION OF THE DRAWINGS

FIG. 4(a) is a top view of a top cover plate in accordance with a preferred form of the invention.

FIG. 4(b) is a side view of the top cover plate in a closed position.

FIG. 4(c) is a side view of the top cover plate in an open position.

FIG. 6(a) is a side view of an applicator nozzle in accordance with a preferred form of the present invention.

FIG. 6(b) is a bottom view of an applicator nozzle in accordance with a preferred form of the invention.

DESCRIPTION OF THE PREFERRED EMBODIMENT

Figure 1:
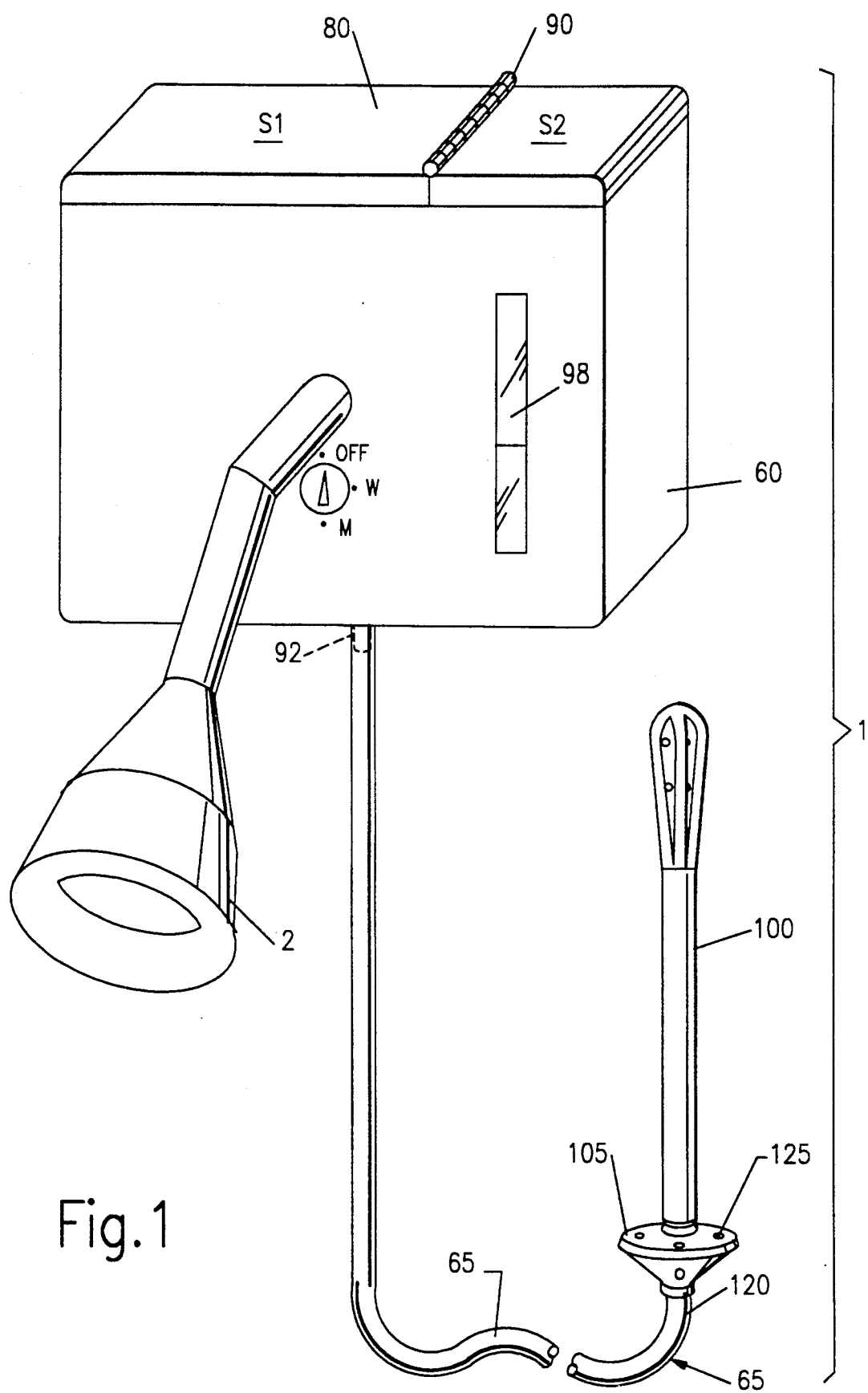
FIG. 1 is an illustration of a vaginal cleansing device embodying a preferred form of the invention.

Turning in detail to the drawings, FIG. 1 provides an illustration of a vaginal cleansing device 1 in accordance with a preferred form of the invention. As shown, the vaginal cleansing device 1 is constructed to be interposed between a shower head 2 and an associated water line (not shown).

Figure 2:
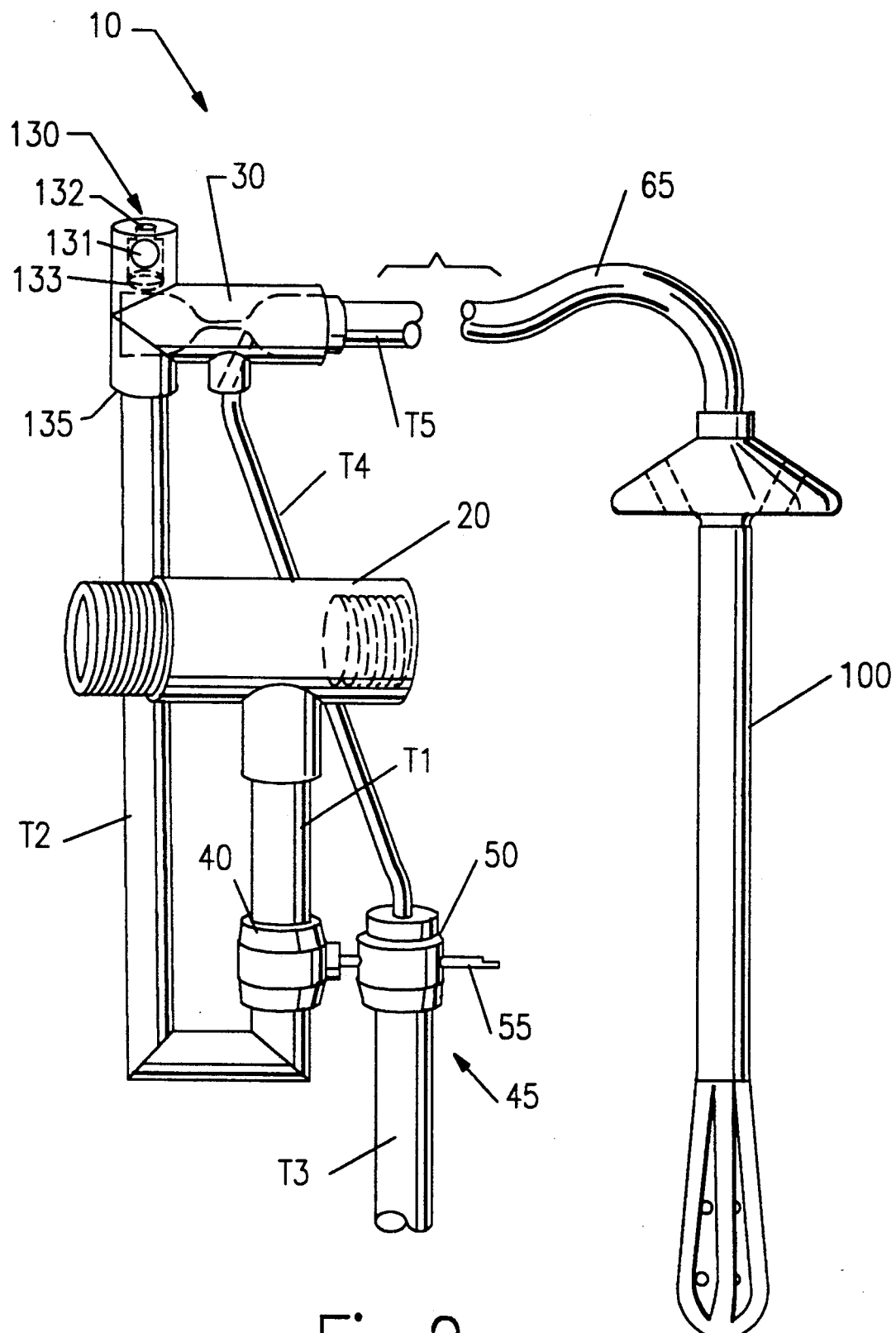
FIG. 2 is a side view of an internal plumbing network of a vaginal cleansing device embodying a preferred form of the invention.

FIG. 2 comprises an expanded side view of the internal plumbing network 10 of the vaginal cleansing device 1. As shown, the internal plumbing network 10 comprises a T-shaped coupling 20, a Venturi 30, a first valve 40, a second valve 50, and an internal tubing network T1-5. The T-shaped coupling 20 is adapted to be interposed between a shower head 2 (shown in FIG. 1) and an associated water source line (not shown) such that a portion of the water delivered to the shower head by the source line may be diverted to the internal plumbing network 10 of the Vaginal cleansing device. A first tubing member T1 of the internal tubing network T1-5 delivers the diverted water to a first valve 40 which controls the flow of water through the vaginal cleansing device. When the first valve 40 is placed in an "open" position, water is directed through a second tubing member T2 to the venturi 30. As the water passes through the venturi 30, concentrate is drafted from a concentrate reservoir 70 (shown in FIG. 3) under the control of a second valve 50. Specifically, when the second valve 50 is placed in an "open" position, concentrate is drafted through a third tubing member T3 from the concentrate reservoir 70 (shown in FIG. 3) to the second valve 50, through the second valve 50, and to the venturi 30 through a fourth tubing member T4. When the second valve 50 is placed in the "closed" position, the drafting is prevented. Last, the solution exiting the venturi 30, which comprises either pure water or a mixture of water and concentrate depending upon the position of the second valve 50, is directed through a fifth tubing member T5 to a solution delivery tube 65 which, in turn, directs the solution to an applicator nozzle 100 (shown in FIGS. 6(a) and 6(b)).

As illustrated, in the preferred form the first valve 40 and the second valve 50 comprise a unitary valve assembly 45 and are controlled by a common stem 55. Specifically, the first valve 40 comprises a first half turn valve which is fully open from 90 to 180 degrees, and the second valve 50 comprises a second half turn valve which is fully open only at 180 degrees.

Figure 3:
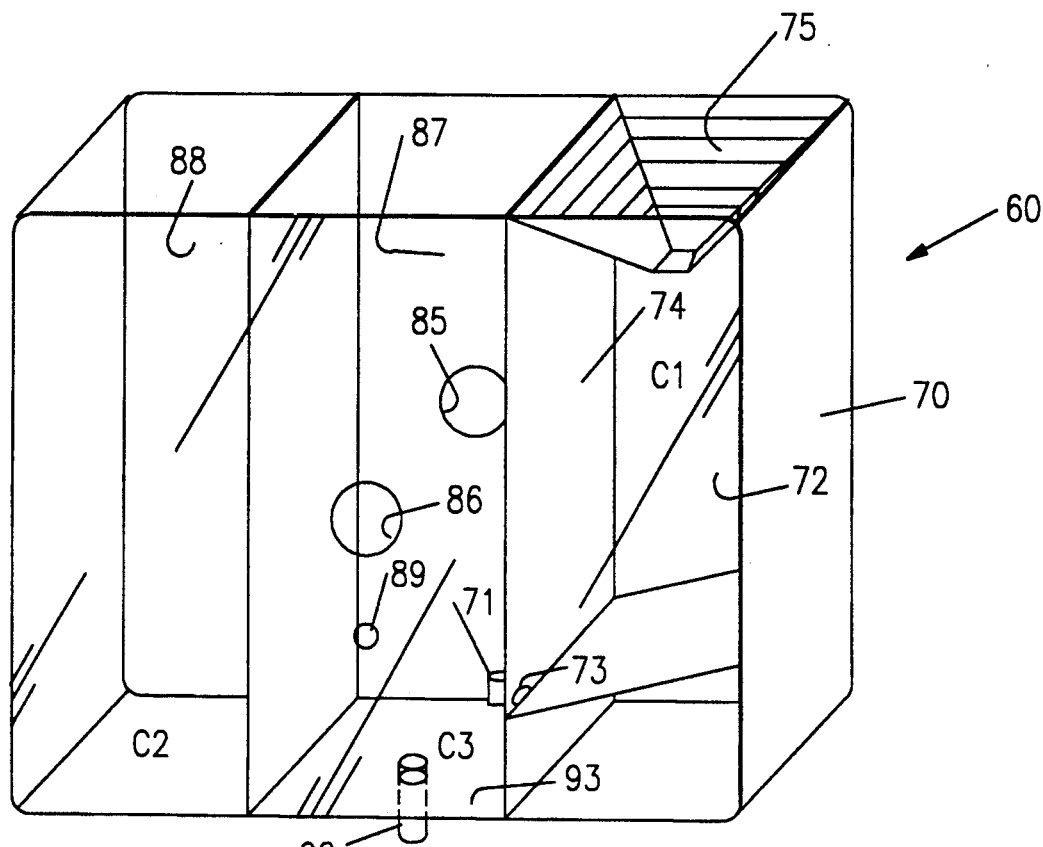
FIG. 3 is a front view of a main body portion of a casing assembly in accordance with a preferred form of the invention.

Turning now to FIGS. 3, 4(a)-(c), and 5, in another preferred form the vaginal cleansing device further comprises a visually attractive casing assembly 60 which comprises a plurality of compartments C1-3. As shown in FIG. 3, a first compartment C1 of the casing assembly 60 comprises a concentrate reservoir 7 which is in communication with the third tubing member T3. Specifically, the third tubing member T3 is coupled to a drain port 71 located at a base region 73 of the reservoir wall 74. In addition, the concentrate reservoir 70 includes an upper funnel shaped section 75, which facilitates filling of the reservoir 70, and a clear plastic front section (not shown) which provides a means for viewing the level of concentrate in the concentrate reservoir 70. A second compartment 02 of the casing assembly 60 comprises a partially enclosed storage area for storing the solution delivery tube 65 (shown in FIGS. 1 and 2) and the applicator nozzle 100 (shown in FIGS. 6(a) and 6(b)) when the cleansing device is not in use, and a third compartment C3 comprises a housing for the internal plumbing network 10. As shown, the third compartment C3 is adapted to pass a water source line (not shown) or the T-shaped coupling 20 through a hole 85 located in its back wall 87, adapted to pass the T-shaped coupling 20 or a shower head stem through a first hole 86 located in its front wall 88, adapted to pass the common valve stem 55 through a second hole 89 also located in the front wall 88, and adapted to pass the solution delivery tube 65 through a fitting 92 located in its base wall 93.

As shown in FIGS. 4(a)-(c), the casing assembly also comprises a top cover plate 80. The top cover plate 80 comprises two sections S1 and S2. The first section S1 is rectangular in shape and is adapted to fit over the second and third compartments C2 and C3 of the casing assembly 60. The first rectangular section S1 is coupled to the second section S2 by a hinge 90. The second section S2 is adapted to form a lid over the concentrate reservoir 70 and may be pivoted upward and folded over onto the first section S1 to provide access to the concentrate reservoir 70.

Figure 5:
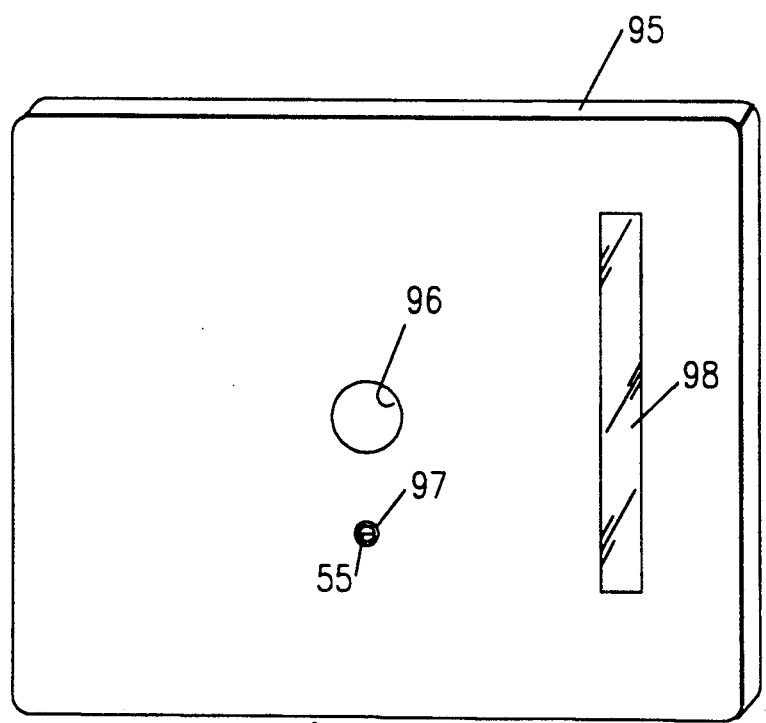
FIG. 5 illustrates a front cover plate in accordance with a preferred form of the invention.

FIG. 5 illustrates a front cover plate 95 of which the casing assembly 60 is further comprised. As shown, a rectangular window 98 is located in a portion of the front cover plate 95 which overlies a clear plastic front portion 72 of the concentrate reservoir 70, thus allowing the level of concentrate remaining in the concentrate reservoir 70 to be viewed through the front cover plate 95. In addition, a first hole 96 and a second hole 97 are located in the front cover plate 95. The first hole 96 is adapted to pass a pipe leading from the T-shaped coupling 20 to the shower head 2 (shown in FIG. 1), and the second hole 97 is adapted to pass the valve stem 55 (shown in FIG. 2) which controls the first and second valves 40 and 50

Turning to FIGS. 6(a) and 6(b), the applicator nozzle 100 of the cleansing device comprises a flared base portion 105, a hollow cylindrical body 110, and a grooved bulbous head 115. As shown, the bulbous head 115 further comprises a plurality of holes 117, which allow the cleansing solution to pass from the applicator nozzle 100 into a user's vagina. Also, the flared base portion 105 is adapted to engage a distal end 120 of the solution delivery tube 65, such that during use the applicator nozzle 100 is in fluid communication with the solution delivery tube 65, but after use the applicator nozzle 100 may be removed for cleaning. In addition, a plurality of holes 125 are located in the flared base portion 105 of the applicator nozzle 100. These holes 125 insure that a seal does not result between the flared base portion 105 of applicator nozzle 100 and the tissue of the user's vagina during use.

Last, referring again to FIG. 2, in still another preferred form, the tubing network T1-5 further comprises a floating ball vacuum breaking device 130 which is deployed adjacent to the water inlet port 135 of the venturi 30. The vacuum breaking device 130 insures complete drainage of the solution delivery tube 65 and nozzle 100 by allowing air to enter the tubing network T1-5 after the cleansing device is turned off by placing the first valve 40 in the closed position. Specifically, when the first valve 40 is placed in the closed position the pressure exerted on the ball 131 by the water in tubing member T2 subsides, the ball 131 falls into the basket 133, and air is allowed to enter the internal plumbing network 10 of the cleansing device 1 through an air intake port 132. In addition, by allowing air to enter the internal plumbing network 10 of the device upon the cessation of water flow through the network 10 the vacuum breaking device 130 insures that, in the event that the flow of water from the source line (not shown) is interrupted, pure concentrate will not be siphoned from the concentrate reservoir 70 and delivered to the user's vagina.

While the invention is susceptible to various modifications and alternative forms, specific examples thereof have been provided in the drawings and are herein described in detail. It should be understood, however, that it is not intended to limit the invention to the particular form disclosed, but on the contrary, the invention is to cover all modifications, equivalents, and alternatives falling within the scope of the invention as defined by the appended claims.

What is claimed is:

1. A vaginal cleansing device comprising a T-shaped coupling, a venturi, a floating ball vacuum breaking device, a concentrate reservoir, an internal tubing network, a first valve, a second valve, a solution delivery tube, an applicator nozzle, and a casing assembly;

the T-shaped coupling being adapted to be interposed between a shower head and an associated water source line for providing a flow of water to the shower head, and the T-shaped coupling being adapted to divert a portion of the water flowing from the source line to the first valve through a first tubing member of the internal tubing network;

the first valve being adapted to control the flow of water through the cleansing device and being in fluid communication with the venturi through a second tubing member of the internal tubing network the venturi being in fluid communication with the solution delivery tube through a third tubing member of the internal tubing network and being adapted to draft a concentrate solution from the concentrate reservoir through a fourth and a fifth tubing member of the internal tubing network;

the second valve being deployed between the fourth and fifth tubing members and adapted to control the flow of concentrate solution from the concentrate reservoir to the venturi;

the first and second valves comprising a unitary valve assembly and being controlled by a common stem, the first valve comprising a first half turn valve which is fully open when the common stem is turned from 90 to 180 degrees, and the second valve comprising a second half turn valve which is fully open only when the common stem is turned to 180 degrees;

the solution delivery tube being in fluid communication with the applicator nozzle for delivering a cleansing solution comprising either water or a mixture of water and concentrate from the venturi to the applicator nozzle;

the applicator nozzle being adapted to pass the cleansing solution;

the casing assembly having a plurality of compartments, a first compartment of which comprises an enclosed area for storing the applicator nozzle and solution delivery tube, and a second compartment of which comprises the concentrate reservoir; and the floating ball vacuum breaking device being deployed adjacent to an inlet port of the venturi and adapted to allow air to enter the cleansing device and to prevent the drafting of concentrate solution by the venturi when the first valve is positioned in a closed position or when the flow of water from the water source line is interrupted.

2. The vaginal cleansing device of claim 1 wherein the concentrate reservoir comprises a plurality of walls including a front wall comprising a clear plastic window, the casing assembly further comprises a top cover plate and a front cover plate, the top cover plate comprising two sections joined by a hinge, one section being adapted to be pivoted at the hinge to provide access to the concentrate reservoir, and the front cover plate has a rectangular window located in its surface to provide a means for viewing the level of concentrate in the concentrate reservoir.

3. A vaginal cleansing device comprising:

a T-shaped coupling, a venturi, a concentrate reservoir, a first valve, a second valve, a solution delivery tube, and an applicator nozzle;

the T-shaped coupling being adapted to be interposed between a shower head and an associated water source line for providing a flow of water to the shower head, the T-shaped coupling being adapted to divert a portion of the water flowing from the source line to the first valve;

the first valve being in fluid communication with the venturi and being adapted to control the flow of water through the cleansing device;

the venturi being in fluid communication with the solution delivery tube and being adapted to draft a concentrate solution from the concentrate reservoir;

the second valve being interposed between the venturi and the concentrate reservoir and being adapted to control the flow of concentrate solution from the concentrate reservoir to the venturi; comprising a first half-turn valve which is fully open when the common stem is turned from 90° to 180°, and said second valve comprising a second half-turn valve which is fully open only when the common stem is turned to 180°;

the solution delivery tube being in fluid communication with the venturi and the applicator nozzle and being capable of delivering a cleansing solution comprising either water or a mixture of water and concentrate from the venturi to the applicator nozzle; and the applicator nozzle being adapted to pass the cleansing solution.

* * * * *